United States Patent

Okabe et al.

[11] Patent Number: 4,824,856
[45] Date of Patent: Apr. 25, 1989

[54] METHOD OF PROTECTING GASTROINTESTINAL TRACT

[75] Inventors: Susumu Okabe, Kyoto; Masaru Satoh, Koshigaya; Tomio Yamakawa, Kashiwa; Yutaka Nomura, Noda; Masatoshi Hayashi, Ichigaya-dai, all of Japan

[73] Assignee: Nippon Chemiphar Co., Ltd., Tokyo, Japan

[21] Appl. No.: 896,154

[22] Filed: Aug. 13, 1986

[30] Foreign Application Priority Data

Aug. 14, 1985 [JP] Japan .................................. 60-178951
Apr. 11, 1986 [JP] Japan .................................. 61-82268

[51] Int. Cl.$^4$ ........................................... A61K 31/415
[52] U.S. Cl. .................................................... 514/395
[58] Field of Search ........................................ 514/395

[56] References Cited

U.S. PATENT DOCUMENTS 4,359,465 11/1982 Ruwart ............................. 514/395

Primary Examiner—Frederick E. Waddell
Attorney, Agent, or Firm—Gerald J. Ferguson, Jr.

[57] ABSTRACT

A method of protecting gastrointestinal tract in a mammal from the untoward, non-gastric-acid-induced effects of exposure to gastrointestinally injuruous agents, which comprises administering orally to said mammal a non-antisecretory amount of a benzimidazole derivative having the formula (I):

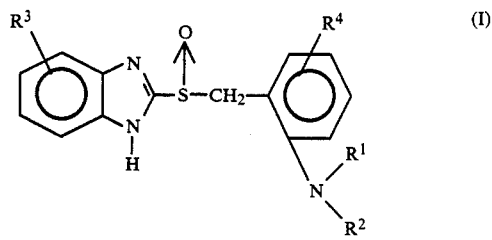

wherein $R^1$ is the hydrogen atom, an alkyl group having 1 to 8 carbon atoms, a cycloalkyl group, phenyl group or aralkyl group, $R^2$ is the hydrogen atom or a lower alkyl group, or $R^1$ and $R^2$ together with the adjacent nitrogen atom forms a ring, and each of $R^3$ and $R^4$ independently is the hydrogen atom, a halogen atom, the trifluoromethyl group, a lower alkyl group, a lower alkoxy group, a lower alkoxycarbonyl group or an amino group.

7 Claims, No Drawings

METHOD OF PROTECTING GASTROINTESTINAL TRACT

BACKGROUND OF THE INVENTION

1. Field of the Invention

This invention relates to a novel cytoprotective agent and a method of protecting gastrointestinal tract in a mammal from the untoward, non-gastric-acid-induced effects of exposure to gastrointestinally injuruous agents.

2. Description of Prior Arts

As agents showing cytoprotective action on gastrointestinal tract, prostaglandin derivatives are heretofore known as described in U.S. Pat. Nos. 4,083,998, 4,081,553 and 4,097,603. Further known is that certain pyridylmethylsulfinylbenzimidazoles such as 2-[(3,5-dimethyl-4-methoxypyridin-2-yl)methylsulfinyl]-5-methoxybenzimidazole (namely, omeprazole) are effective as cytoprotective agents as described in Japanese Patent Provisional Publication No. 57(1982)-53406 (corresponding to U.S. Pat. No. 4,359,465).

As shown in the above patent publications, the cytoprotective agent is effective in the treatment and prevention of gastrointestinal inflammatory diseases occurring from various causes. These inflammatory diseases are non-gastric-acid-induced inflammatory diseases such as gastric inflammatory diseases, for example, gastritis, and intestinal inflammatory diseases, for example, Crohn's diseases, inflammatory bowel diseases, infectious centeritis, colitis, ulcerative colitis, pseudomembranous colitis, diverticulitis, and allergenic and radiological inflammatory diseases.

These inflammatory diseases are known to be caused by a wide variety of substances existing in gastrointestinal tract. Examples of the substances include microorganisms (e.g., viruses and fungi), bacterial toxins, and chemical agents. These substances are apt to attack the lining of the gastrointestinal tract and producing the inflammatory state.

The aforementioned prostaglandin derivatives and heterocyclic alkylsulfinylbenzimidazoles such as 2-[(3,5-dimethyl-4-methoxypyridin-2-yl)methylsulfinyl]-5-methoxybenzimidazole are both known as showing both of cytoprotective action and inhibitory action on secretion of gastric acid. In more detail, these compounds show cytoprotective action when used in a small dose and also show inhibitory action on secretion of gastric acid when used in a large amount.

Nevertheless, the inhibitory action on secretion of gastric acid and the cytoprotective action are different actions being independent of each other, as is described by Robert et al in "Cytoprotection by Prostaglandins in Rats", Gastroenterology, 77, 433–443(1979).

The present inventors previously have discovered that a novel benzimidazole derivative having the formula (I):

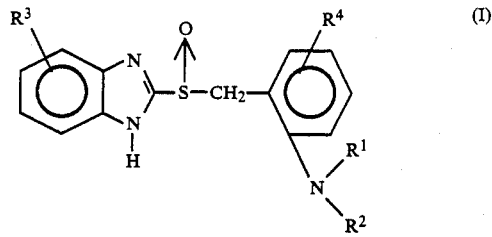

wherein $R^1$ is the hydrogen atom, an alkyl group having 1 to 8 carbon atoms, a cycloalkyl group, phenyl group or aralkyl group, $R^2$ is the hydrogen atom or a lower alkyl group, or $R^1$ and $R^2$ together with the adjacent nitrogen atom forms a ring, and each of $R^3$ and $R^4$ independently is the hydrogen atom, a halogen atom, the trifluoromethyl group, a lower alkyl group, a lower alkoxy group, a lower alkoxycarbonyl group or an amino group, shows prominent inhibitory action on secretion of gastric acid and accordingly have proposed such compounds per se, and processes of the preparation and use of the same in Japanese Patent Applications Nos. 59(1984)-182400, 60(1985)-61194, and 60(1985)-61195 (corresponding to U.S. patent application Ser. No. 767,424 and GB No. 2,163,747A).

SUMMARY OF THE INVENTION

As a result of further study on the benzimidazole derivatives of the formula (I), the present inventors now have discovered that these derivatives show not only the above-mentioned inhibitory action on secretion of gastric acid but also the cytoprotective action for gastrointestinal tract.

Accordingly, an object of the present invention is to provide a novel cytoprotective agent for gastrointestinal tract.

Another object of the invention is to provide a method of protecting gastrointestinal tract in a mammal from the untoward, non-gastric-acid-induced effects of eposure to gastrointestinally injuruous agents.

There is provided by the present invention a method of protecting gastrointestinal tract in a mammal from the untoward, non-gastric-acid-induced effects of exposure to gastrointestinally injuruous agents, which comprises administering orally to said mammal a non-antisecretory amount (that is, less than antisecretory $ED_{50}$) of a benzimidazole derivative having the formula (I):

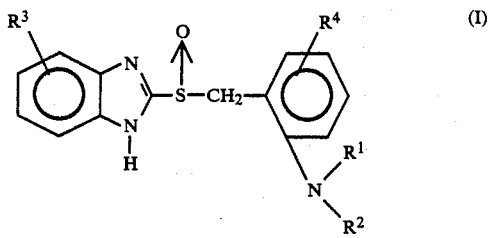

wherein $R^1$ is the hydrogen atom, an alkyl group having 1 to 8 carbon atoms, a cycloalkyl group, phenyl group or aralkyl group, $R^2$ is the hydrogen atom or a lower alkyl group, or $R^1$ and $R^2$ together with the adjacent nitrogen atom forms a ring, and each of $R^3$ and $R^4$ independently is the hydrogen atom, a halogen atom, the trifluoromethyl group, a lower alkyl group, a lower alkoxy group, a lower alkoxycarbonyl group or an amino group.

The benzimidazole derivative of the formula (I) which is the active ingredient of the cytoprotective agent of the invention can be prepared by the process according to the following equation:

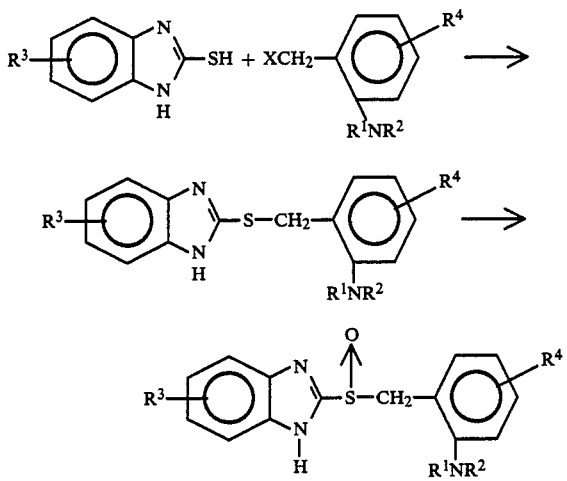

wherein X is a reactive group and each of $R^1$ to $R^4$ has the same meaning as defined hereinbefore.

Representative examples of the compounds of the formula (I) include:

Compound 1: 2-(2-dimethylaminobenzylsulfinyl)benzimidazole,
Compound 2: 2-(2-diethylaminobenzylsulfinyl)benzimidazole,
Compound 3: 2-(2-aminobenzylsulfinyl)benzimidazole,
Compound 4: 2-(2-methylaminobenzylsulfinyl)benzimidazole,
Compound 5: 2-(2-dimethylaminobenzylsulfinyl)-5-methoxybenzimidazole,
Compound 6: 2-(2-diethylaminobenzylsulfinyl)-5-methoxybenzimidazole,
Compound 7: 2-(2-dimethylamino-6-methylbenzylsulfinyl)benzimidazole,
Compound 8: 2-(2-dimethylaminobenzylsulfinyl)-5-methoxycarbonylbenzimidazole,
Compound 9: 2-(2-dimethylaminobenzylsulfinyl)-5-methylbenzimidazole,
Compound 10: 5-chloro-(2-dimethylaminobenzylsulfinyl)benzimidazole,
Compound 11: 5-amino-(2-dimethylaminobenzylsulfinyl)benzimidazole,
Compound 12: 2-(2-dimethylamino-5-methoxybenzylsulfinyl)benzimidazole,
Compound 13: 2-(2-dimethylamino-5-methylbenzylsulfinyl)benzimidazole,
Compound 14: 2-(2-piperidinobenzylsulfinyl)benzimidazole,
Compound 15: 2-[2-(N-cyclohexyl-N-methylamino)benzylsulfinyl]benzimidazole, and
Compound 16: 2-[2-(N-benzyl-N-methylamino)benzylsulfinyl]benzimidazole.

The benzimidazole derivative employed in the present invention preferably is a compound having the formula (I) wherein $R^1$ is an alkyl group containing 1-8 carbon atoms. $R^2$ preferably is a lower alkyl group. $R^3$ preferably is the hydrogen atom or an alkoxy group. $R^4$ preferably is the hydrogen atom or a lower alkyl group.

In the specification, the lower alkyl group and the lower alkoxy group mean those containing 1-6 carbon atoms.

The benzimidazole derivative of the invention has been confirmed to show a prominent effect in a test for evaluating cytoprotective action for gastrointestinal tract, that is, a test for evaluation of protection of stomach skin (i.e., lining) from damage (i.e., erosion) caused by etnalnol containing hydrochloric acid. This test for evaluation of protection of stomach surface from damage using a combination of ethanol and hydrochloric acid is based on introduction of highly concentrated hydrochloric acid into a stomach from outside. Accordingly, this test is appropriate for evaluating a function of a test compound introduced into the stomach in disregard of influence of secretion of gastric acid.

In the above-mentioned test using rat, linear or striped damages were observed on the mucousa of glandular portion, after one hour of administration of hydrochloric acid-ethanol. It has been further confirmed that the benzimidazole derivative of the formula (I), namely, the active ingredient of the invention, is effective for suppression of such damage depending upon the introduced dose.

Accute toxicity of the benzimidazole derivative of the formula (I) has been determined in oral administration. It has been confirmed by observation of three days after oral administration to ICR male mouse (23-26 g) that 2-(2-dimethylaminobenzylsulfinyl)benzimidazole, which is one of representative compounds of the active ingredient of the invention, shows MLD of more than 1,000 mg/kg.

Accordingly, it has been confirmed that the benzimidazole derivative of the invention is of value as a cytoprotective agent for gastrointestinal tract and can be utilized for the treatment or prevention of a non-gastric-acid-induced, non-traumatically-induced, non-neoplastic gastrointestinal inflammatory disease in a mammal suffering from or particularly susceptible to the development of said disease, as disclosed in U.S. Pat. No. 4,359,465 (Ruwart).

It is known in the art concerned that "a mammal susceptible to the development of said disease" is such mammal that takes a large amount of alcoholic drinks daily, is exposed to electromagnetic waves at a level of causing destruction of cell, is exposed to cell-destructing chemicals, for instance, through taking a large amount of the chemical or taking continuously the chemicals, or exposed to pathogenic microorganisms. It is also known that a mammal having a great number of anamnesis such as gastric ulcer and duodenal ulcer is sesceptible to inflammatory disease.

The cytoprotective agent of the invention is of value not only for preventing and treating these inflammatory diseases, but also for decreasing the rate of occurrence and degree of ulcer generally caused by these diseases until the ulcer and inflammation is completely cured.

The cytoprotective agent for gastrointestinal tract containing a benzimidazole derivative of the formula (I) is administered orally. Examples of the preparation forms for oral administration include tablets, capsules powder, granules, and syrup. In the formulation of these preparations, there can be used excipients, disintegrants, binders, lubricants, pigments, diluents and the like which are commonly employed in the art. Examples of the excipients include dextrose and lactose. Examples of the disintegrants include starch and carboxymethylcellulose. Examples of the lubricants include magnesium stearate and talc. Examples of the binders include hydroxypropylcellulose, gelatin and polyvinylpyrrolidone.

The dose is generally not more than 500 mg/day, preferably about 100 μg/day to 300 mg/day, for an adult. The dose can be either increased or decreased depending upon the age and other conditions.

The compound of the present invention shows the cytoprotective action in an amount of approx. one thirds of that of omeprazole, known cytoprotective agent, as evidenced by the below-mentioned results in the test for evaluation of cytoprotective action against hydrochloric acid-ethanol-induced gastric damage. In more detail, it has been experimentally confirmed that 2-(2-dimethylaminobenzylsulfinyl)benzimidazole included in the compound of the invention shows at a dose of 10 mg/kg almost the same cytoprotective effect as that of the omeprazole at a dosage of 30 mg/kg when both compounds are administered 6 hours or 12 hours in advance of the administration of ethanol and hydrochloric acid.

In view of the facts that the known omeprazole shows sufficient cytoprotective effect in a dose of one tens (1/10) of a dose required for suppressing secretion of gastric acid (Japanese Patent Provisional Publication No. 57(1982)-53406 corresponding to U.S. Pat. No. 4,359,465), and that the compound of the invention shows almost the same suppressive action of secretion of gastric acid as the omeprazole, in combination of the above-described experimental results, it is apparent that the compound of the present invention shows sufficient cytoprotective action at a dose of less than 1/30 of that required to show a suppressive action on secretion of gastric acid. This means that the compound of the invention is a marked cytoprotective compound.

The present invention is further described by the following examples.

EXAMPLE 1

Synthesis of 2-(2-Dimethylaminobenzylsulfinyl)benzimidazole (1) 2-(2-Dimethylaminobenzylthio)benzimidazole:

2-Mercaptobenzimidazole (4.73 g) was dissolved in 150 ml of ethanol, and to the solution was added 6.18 g of 2-dimethylaminobenzyl chloride hydrochloride. The mixture was stirred at room temperature for 30 minutes. Precipitated crystals were collected by filtration. A saturated aqueous $NaHCO_3$ solution was added to the crystals, and the resulting mixture was extracted with chloroform. The chloroform layer was washed with saturated brine and then dried over anhydrous sodium sulfate. The solvent was distilled off under reduced pressure and the residue was recrystallized from a mixture of chloroform and acetonitrile to obtain 5.39 g of 2-(2-dimethylaminobenzylthio)benzimidazole as a colorless crystalline product (m.p. 164° C.).

(2) 2-(2-Dimethylaminobenzylsulfinyl)benzimidazole 2-(2-Dimethylaminobenzylthio)benzimidazole (4.8 g) was dissolved in a mixture of 40 ml of chloroform and 5 ml of methanol. After the solution was chilled to 0° C., 3.86 g of m-chloroperbenzoic acid (purity: 70%) was added portionwise. Ten minutes later, a saturated aqueous $NaHCO_3$ solution was added to the reaction mixture, and the resulting mixture was extracted with chloroform. The chloroform solution was washed with saturated brine and then dried over anhydrous sodium sulfate. The chloroform was distilled off under reduced pressure and the residue was recrystallized from a mixture of chloroform and ether to obtain 2.97 g of 2-(2-dimethylaminobenzylsulfinyl)benzimidazole as a colorless crystalline product (m.p. 112° C., decomposed).

$IR\nu_{max}^{KBr}$ cm$^{-1}$: 3170, 1485, 1435, 1400, 1260, 1040

$^1$H-NMR(CDCl$_3$): δ

2.62 (s, 6H, —N(CH$_3$)$_2$)

4.47 & 4.87 (each, d, 2H, J=14 Hz, —SCH$_2$—), 6.70–7.90 (m, 8H, aromatic protons)

12.16 (broad, 1H, —NH)

EXAMPLE 2

The below-mentioned compounds were prepared in almost the same manner as in Example 1:

(a) 2-(2-dimethylaminobenzylsulfinyl)-5-methoxybenzimidazole, m.p. 105° C. (decomp.);

(b) 2-(2-diethylaminobenzylsulfinyl)-5-methoxybenzimidazole, m.p. 110.5°–112° C. (decomp.); and (a) 2-(2-dimethylamino-5-methylbenzylsulfinyl)-5-methoxybenzimidazole, m.p. 141.5°–142.5° C. (decomp.).

EXAMPLE 3

Cytoprotective action on gastrointestinal tract

Male Donryu rats (240–270 g) were fasted for 24 hours. To the rats was given orally a hydrochloric acid-ethanol solution (150 mM HCl in 60% ethanol) was given in a volume of 1 ml/200 g. One hour later, each rat was killed by ether and the stomach was examined for any damage (erosion) in the glandular portion. Length (mm) of each erosion was measured, and total length (mm) of the erosions observed in one rat was calculated. The calculated value was idendified as "erosion index".

Each test compound was suspended in 1% aqueous carboxymethylcellulose solution just before administration, and administered orally in a volume of 0.5 ml/100 g of body weight at 30 minutes, 6 hours, 12 hours, or 24 hours before the hydrochloric acid-ethanol treatment. To the control groups was administered the solvent only.

The suppression ratio was calculated in accordance with the following equation.

$$\text{Suppression ratio (\%)} = \left(1 - \frac{\text{Erosion index (mm) in the case of administration of test compound}}{\text{Erosion index (mm) in the case of administration of no test compound}}\right) \times 100$$

The results are set forth in Table 1.

TABLE 1

| [Effect against Hydrochloric acid-ethanol Erosion] | | | |
|---|---|---|---|
| Test Compound | Dose (mg/kg) | Suppression Ratio (%) | Administration of Test Compound |
| Compound A | 10 | 68** | before 30 min. |
| | 30 | 97*** | before 30 min. |
| Compound B | 10 | 84*** | before 30 min. |
| | 30 | 87*** | before 30 min. |
| Compound C | 10 | 90*** | before 30 min. |
| | 30 | 96*** | before 30 min. |
| Compound D | 10 | 89*** | before 30 min. |
| | 30 | 100*** | before 30 min. |
| Omeprazole | 10 | 21 | before 30 min. |
| | 30 | 74* | before 30 min. |
| Compound D | 10 | 42* | before 6 hrs. |
| | 30 | 100*** | before 6 hrs. |

TABLE 1-continued

[Effect against Hydrochloric acid-ethanol Erosion]

| Test Compound | Dose (mg/kg) | Suppression Ratio (%) | Administration of Test Compound |
|---|---|---|---|
| Omeprazole | 30 | 53** | before 6 hrs. |
| Compound D | 10 | 20 | before 12 hrs. |
|  | 30 | 87*** | before 12 hrs. |
| Omeprazole | 30 | 3 | before 12 hrs. |
| Compound A | 30 | 37* | before 24 hrs. |
|  | 100 | 91* | before 24 hrs. |
| Omeprazole | 100 | 18 | before 24 hrs. |

Remarks:

Significant Difference: * ($p<0.05$)  ($p<0.01$) * ($p<0.001$)

Compound A: 2-(2-dimethylaminobenzylsulfinyl)-5-methoxybenzimidazole;

Compound B: 2-(2-diethylaminobenzylsulfinyl)benzimidazole;

Compound C: 2-(2-dimethylamino-5-methylbenzylsulfinyl)-5-benzimidazole;

Compound D: 2-(2-dimethylaminobenzylsulfinyl)-benzimidazole;

Omeprazole: 2-[(3,5-dimethyl-4-methoxypyridin-2-yl)methylsulfinyl]-5-methoxybenzimidazole.

EXAMPLE 4

Inhibitory effects on secretion of gastric acid

Male Donryu rats (200-250 g) were fasted (while allowing free access to water) for 24 hours in accordance with the conventional method [Shay, H. et al., Gastroenterology, 5, 43-61 (1945)]. Under ether anesthesia the rat was abdominally sectioned. The pylorus was then ligated and each test compound was administered orally. Three hours later, each rat was killed and the stomach was removed to collect the gastric juice. The inhibitory effect was determined by comparing the acid output which was obtained by titration to pH 7.0 with 0.1-N NaOH by means of an automatic titrator.

The above-mentioned Compound D showed the inhibitory effect of 61% at dose of 10 mg/kg, while Omeprazole showed the inhibitory effect of 67% at dose of 10 mg/kg.

| Example 5: Preparation in the form of pellet | |
|---|---|
| A pellet (220 mg) containing: | |
| active component | 50 mg |
| lactose | 103 mg |
| starch | 50 mg |
| magnesium stearate | 2 mg |
| hydroxypropylcellulose | 15 mg |
| was obtained. | |
| Example 6: Preparation in the form of capsule | |
| A gelatin-shell hard capsule containing 350 mg of the core portion consisting of: | |
| active component | 40 mg |
| lactose | 200 mg |
| starch | 70 mg |
| polyvinylpyrrolidone | 5 mg |
| crystalline cellulose | 35 mg |
| was obtained. | |
| Example 7: Preparation in the form of granules | |
| One gram of granules containing: | |
| active component | 200 mg |
| lactose | 450 mg |
| corn starch | 300 mg |
| hydroxypropylcellulose | 50 mg | was obtained.

We claim:

1. A method of protecting gastrointenstinal tract in a mammal from the untoward, non-gastric-acid-induced effects of exposure to gastrointestinally injuruous agents, which comprises administering orally to said mammal a non-antisecretory amount of benzimidazole derivative having the formula (I):

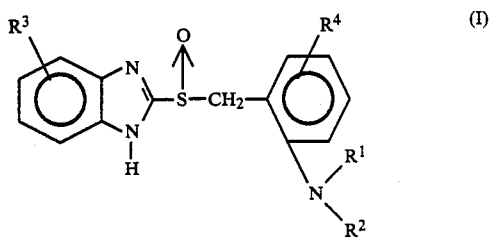

wherein $R^1$ is an alkyl group having 1 to 8 carbon atoms, $R^2$ is an hydrogen atom or a lower alkyl group, and each of $R^3$ and $R^4$ independently is an hydrogen atom, a halogen atom, a trifluoromethyl group, a lower alkyl group, a lower alkoxy group, a lower alkoxycarbonyl group or an amino group.

2. The method as claimed in claim 1, wherein $R^2$ of the formula (I) representing the benzimidazole derivative is a lower alkyl group.

3. The method as claimed in claim 1, wherein $R^3$ of the formula (I) representing the benzimidazole derivative is the hydrogen atom or a lower alkoxy group.

4. The method as claimed in claim 1, wherein $R^4$ of the formula (I) representing the benzimidazole derivative is the hydrogen atom or a lower alkyl group.

5. A method of protecting gastrointenstinal tract in a mammal from the untoward, non-gastric-acid-induced effect of exposure to gastrointestinally injuruous agents, which comprises administering orally to said mammal a non-antisecretory amount of a benzimidazole derivative having the formula (I):

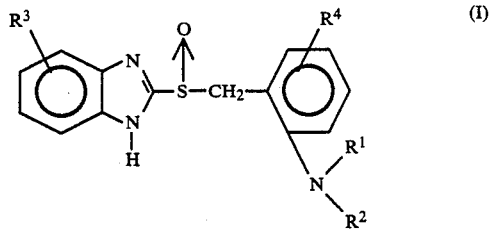

wherein $R^1$ is an hydrogen atom, an alkyl group having 1 to 8 carbon atoms, a cycloalkyl group, phenyl group or an aralkyl group, $R^2$ is a lower alkyl group, and each of $R^3$ and $R^4$ independently is an hydrogen atom, a halogen atom, a trifluoromethyl group, a lower alkyl group, a lower alkoxy group, a lower alkoxycarbonyl group or an amino group.

6. The method as claimed in claim 5, wherein $R^3$ of the formula (I) representing the benzimidazole derivative is an hydrogen atom or a lower alkoxy group.

7. The method as claimed in claim 5, wherein $R^4$ of the formula (I) representing the benzimidazole derivative is an hydrogen atom or a lower alkyl group.

* * * * *